US009140771B2

(12) United States Patent
Carroll et al.

(10) Patent No.: US 9,140,771 B2
(45) Date of Patent: Sep. 22, 2015

(54) IMAGING-BASED DIAGNOSTIC APPARATUS AND METHODS FOR QUANTIFYING CEREBRAL VASCULAR RESERVE

(75) Inventors: Timothy J. Carroll, Chicago, IL (US); Michael Hurley, Chicago, IL (US); Parmede Vakil, Chicago, IL (US); Rajiv Menon, Schaumburg, IL (US); Sumeeth Vijay Jonathan, Manalapan, NJ (US); Renee Qian, Palatine, IL (US); Sameer Ansari, Chicago, IL (US)

(73) Assignee: Northwestern University, Evanston, IL (US)

( * ) Notice: Subject to any disclaimer, the term of this patent is extended or adjusted under 35 U.S.C. 154(b) by 490 days.

(21) Appl. No.: 13/405,126

(22) Filed: Feb. 24, 2012

(65) Prior Publication Data

US 2012/0220858 A1    Aug. 30, 2012

Related U.S. Application Data

(60) Provisional application No. 61/446,843, filed on Feb. 25, 2011.

(51) Int. Cl.
| | |
|---|---|
| *A61B 5/055* | (2006.01) |
| *G01R 33/561* | (2006.01) |
| *G01R 33/563* | (2006.01) |
| *A61B 5/00* | (2006.01) |
| *G01R 33/56* | (2006.01) |

(52) U.S. Cl.
CPC ...... *G01R 33/5616* (2013.01); *G01R 33/56366* (2013.01); *A61B 5/0042* (2013.01); *A61B 5/055* (2013.01); *A61B 2576/026* (2013.01); *G01R 33/5602* (2013.01)

(58) Field of Classification Search
CPC ........ A61B 5/01; A61B 5/0008; A61B 5/455; A61B 8/08; A61B 8/488
USPC ......................................... 600/407, 410, 420
See application file for complete search history.

(56) References Cited

U.S. PATENT DOCUMENTS

| 4,779,619 | A | * | 10/1988 | Winkler ........................ 600/410 |
|---|---|---|---|---|
| 5,304,931 | A | * | 4/1994 | Flamig et al. ................. 324/309 |
| 5,548,216 | A | * | 8/1996 | Dumoulin et al. ............ 324/309 |
| 6,066,949 | A | * | 5/2000 | Alley et al. ................... 324/309 |
| 6,295,465 | B1 | | 9/2001 | Simonetti |

(Continued)

OTHER PUBLICATIONS

Fan et al (Involvement of the anterior cingulate and frontoinsular cortices in rapid processing of salient facial emotional information, Feb. 1, 2011; 54(3): 2539-2546. doi: 10.1016/j.neuroimage.2010.10. 007, NIH Public access, Autor manuscript).*

*Primary Examiner* — Joel F Brutus
(74) *Attorney, Agent, or Firm* — Schiff Hardin LLP

(57) ABSTRACT

In one aspect of the disclosure, an MRI-based system includes an MRI scanner having a first axis and a first plane perpendicular to the first axis, a pulse sequence module configured to provide a 3D pulse sequence to the MRI scanner, and a control module configured to instruct the MRI scanner to conduct radial k-space samples having N second planes that each are perpendicular to the first plane and through which the first axis passes, N being an integer greater than 1. The 3D pulse sequence instructs the MRI scanner to a radio-frequency (RF) pulse, conduct a gradient readout in the first plane, and conduct a gradient readout in one of the N second planes.

5 Claims, 4 Drawing Sheets

(56) References Cited

U.S. PATENT DOCUMENTS

| | | |
|---|---|---|
| 6,546,275 B2 | 4/2003 | Carroll |
| 8,099,149 B2 | 1/2012 | Carroll |
| 2003/0055329 A1* | 3/2003 | Zur .............................. 600/410 |
| 2003/0065258 A1* | 4/2003 | Gupta et al. .................. 600/410 |
| 2004/0085331 A1* | 5/2004 | Sai ................................ 345/634 |
| 2005/0004448 A1* | 1/2005 | Gurr et al. ..................... 600/420 |
| 2007/0249929 A1* | 10/2007 | Jeong et al. ................... 600/410 |
| 2008/0119720 A1 | 5/2008 | Carroll |

\* cited by examiner (A)

(B)

(C)

IMAGING-BASED DIAGNOSTIC APPARATUS AND METHODS FOR QUANTIFYING CEREBRAL VASCULAR RESERVE

CROSS-REFERENCE TO RELATED PATENT APPLICATION

This application claims priority to and the benefit of, pursuant to 35 U.S.C. §119(e), U.S. provisional patent application Ser. No. 61/446,843, filed on Feb. 25, 2011, entitled "An IMAGING-BASED DIAGNOSTIC APPARATUS AND METHODS FOR QUANTIFYING CEREBRAL VASCULAR reserve," by Timothy J. Carroll et al., the disclosure of which is incorporated herein in its entirety by reference.

STATEMENT AS TO RIGHTS UNDER FEDERALLY-SPONSORED RESEARCH

This invention was made with government support under RO NS049395-01 awarded by the National Institutes of Health. The government has certain rights in the invention.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD

The present disclosure is in the field of imaging-based diagnostic apparatus and, in particular, magnetic resonance imaging (MRI)-based systems for quantifying cerebral vascular reserve (CVR).

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Perfusion as related to tissue refers to the exchange of oxygen, water and nutrients between blood and tissue. The measurement of tissue perfusion is important for the functional assessment of organ health. Perfusion weighted images (PWI) show the degree to which tissues are perfused by the change in their brightness as a bolus of contrast agent washes through the vasculature, and can be used to assess the health of brain tissues that have been damaged by a stroke. A number of methods have been used to produce perfusion images using magnetic resonance imaging techniques. One technique, as exemplified by U.S. Pat. No. 6,295,465, is to determine the wash-in or wash-out kinetics of contrast agents such as chelated gadolinium. From the acquired NMR data, images are produced which indicate cerebral blood flow (CBF), cerebral blood volume (CBV), and mean transit time (MTT) at each voxel. Each of these perfusion indication measurements provides information that is useful in diagnosing tissue health.

Bolus tracking cerebral perfusion has expansive use in the clinical setting for imaging a variety of diseases including cerebrovascular occlusive disease, stroke, central nervous system tumors, and Alzheimer's disease. Parametric images of cerebral perfusion are calculated by analyzing the tracer kinetics of a known contrast agent, whether it is radio-labeled water in positron emission tomography (PET), an iodinated contrast agent in computed tomography (CT), spin-labeled water in arterial spin labeling MRI, or a paramagnetic contrast agent in dynamic susceptibility contrast (DSC) MRI. While the standard for quantification of cerebral perfusion still remains radio-labeled PET imaging, the requirement of a cyclotron for production of the radio-labeled tracer limits the availability of the technique. CT has the potential to quantify perfusion; however, iodinated contrast agents and large doses of radiation are required in this imaging method. This is problematic for frequent follow-up scan session as well as the use of the method in certain patient populations, such as young children.

MR-based perfusion imaging methods produce parametric images that only convey information relating to relative, and not quantitative, cerebral blood flow (rCBF) and cerebral blood volume (rCBV). Current methods for creating quantitative measurements of perfusion from MR imaging data rely on assuming population averaged values of normal appearing white matter (WM) and by setting the CBF values in this tissue to a preset value. This method has a poor correlation to PET imaging standards. Instead, a method which determines the quantitative CBF and CBV (qCBF and qCBV, respectively) on a subject-by-subject basis would be preferred.

Ischemic stroke is the third leading cause of death and disability in the industrialized world. In the US alone, between 500,000 and 750,000 people are affected by stroke each year. In an ischemic stroke, blood flow to parts of the brain is reduced below the metabolic needs and neuronal cell death ensues. Intracranial atherosclerosis is considered the leading cause of stroke worldwide. Intracranial atherosclerosis is caused by the accumulation of cholesterol plaque in the wall of an artery, causing progressive narrowing (stenosis) or complete blockage. Early detection and treatment of an intracranial stenosis has the potential to prevent a stroke. There is high rate of stroke in cases of stenosis greater that 70% despite maximal medical therapy. Conversely, many patients develop adequate collateral circulation to compensate for even severe stenosis without the need for intervention.

There is currently no robust way to evaluate the degree to which individuals are able to compensate for the presence of an intracranial stenosis, an extra-cranial stenosis, trauma, vascular malformations, etc. Angioplasty and stenting of stenosis may help patients with insufficient collateral flow, but the procedure carries a significant risk indicating the need for a more definitive method of identifying patients who will benefit from it.

Therefore, an objective measurement of the adequacy of cerebral perfusion downstream to the lesion should be central to treatment decision making Studies of relative perfusion with a stress challenge (i.e. Acetezolemide) are well known but are subjective and limited by the high likelihood of contralateral disease.

The viability of the brain parenchyma depends on the ability of the blood supply to adequately perfuse the tissue. In an ischemic stroke, blood flow to parts of the brain is reduced below the metabolic needs and neuronal cell death ensues. Atherosclerosis caused by the accumulation of cholesterol plaque in the wall of an artery in the arteries of the neck and head, is considered the leading cause of stroke worldwide. There is a high rate of stroke in cases of progressive narrowing (stenosis) of the arteries of the head and neck greater that 70% despite maximal medical therapy. Conversely, many patients develop adequate collateral circulation to compensate for even severe stenosis or complete blockage (occlusion) without the need for intervention. In a setting of vascular disease the ability to compensate for vascular disease is reduced although symptoms of the decrease symptoms are not observable. In patients with cerebrovascular disease, a higher risk of stroke is associated with inability to regular cerebral blood flow quantified by Cerebro-vascular Reserve (CVR).

The progression of cerebrovascular disease can be characterized in terms of three stages of hemodynamic failure. The three stages reflect the ability of the arteries of the head to compensate to the presence of a flow limiting stenosis in the head/neck. In this model the severity of compromise, i.e. the stage is reflected in changes in the cerebral blood volume, cerebral blood flow and oxygen extraction of the affected brain. In patients in the final stages of hemodynamic failure (stage III), it is found that Oxygen Extraction Fraction (OEF) was increased by as much has 50% relative to Stage I or Stage II failure. The increases of OEF values were measured with positron emission tomography scans and were able to predict which patients were likely to have a stroke. In other words, determining the stage of hemodynamic failure will likely provide a tool by which more aggressive management of atherosclerosis can help prevent a stroke. Although very useful, the need for an on-site cyclotron for the production of the specific radioactive tracer has limited this approach to a handful of research hospitals.

There have been a number of imaging approached to quantify CVR with a ACZ challenge. Compute tomography (CT) perfusion using Xe has been studied for over 20 years in evaluating cerebral perfusion. Xe-CT requires the presence of an anesthetist due to the pharmacologic and side effects of Xe inhalation which include headache, vomiting, decrease respiratory rate and convulsion. Xe-CT is not currently approved for use by the US FDA.

A more recent approach to CT perfusion involves tracking a bolus of contrast agent as if flows through the head. CT perfusion exposed the patient to high doses of radiation and quantitative values have not been shown to be robust. In the prevention of stroke, where two scans and periodic follow up may be required, the cumulative radiation dose should be minimized.

A recognized reference standard for quantitative cerebral perfusion is positron emission tomography (PET). Unlike standard FDG-PET scans, PET perfusion and OEF measurements require an on-site cyclotron to produce the short half life (122.24 s) radioactive tracer. The need for the cyclotron has limited PET perfusion to use at a fewer than 10 research sites in the US.

While technically not an imaging modality, it is possible measure global (i.e. hemispheric) changes in CVR measures with ACZ via transcranial Doppler ultrasonography of the middle cerebral artery. It may be less sensitive to detect compromised CVR than direct measurement of cerebral perfusion by Xe/CT (useful but single hemisphere).

Therefore, a heretofore unaddressed need exists in the art to address the aforementioned deficiencies and inadequacies.

SUMMARY

In one aspect, the present disclosure relates to an MRI-based system. In one embodiment, the MRI-based system includes an MRI scanner having a first axis and a first plane perpendicular to the first axis, a pulse sequence module configured to provide a 3D pulse sequence to the MRI scanner, and a control module configured to instruct the MRI scanner to conduct radial k-space samples having N second planes that each are perpendicular to the first plane and through which the first axis passes, N being an integer greater than 1. The 3D pulse sequence instructs the MRI scanner to generate a radio-frequency (RF) pulse, conduct a gradient readout in the first plane, and conduct a gradient readout in one of the N second planes.

In one embodiment, the control module is configured to instruct the MRI scanner to conduct an echo-planar readout along the first axis. In another embodiment, the control module is configured to instruct the MRI scanner to sample the k-space volume over a plurality of sample points sampling a line perpendicular to the first axis. In yet another embodiment, the control module is configured to instruct the MRI scanner to acquire k-space samples through a 3D k-space volume at oblique angles so as to trace out samples oriented radially in the N second planes. In a further embodiment, the control module is configured to instruct the MRI scanner to conduct a first set of N consecutive gradient readouts for the N second planes, where the MRI scanner is configured to have a raw sampling window about from 10,000 ms to 10 seconds.

Further, the MRI-based system may comprise an imaging module configured to construct a first 3D image frame using readout results of the first set of readouts. In one embodiment, the imaging module is configured to construct images with a spatial resolution about 2.5 mm×0.825 mm×0.825 mm. In another embodiment, the imaging module is configured to construct 3D images at a rate of about 0.6 second/frame.

In one embodiment, the control module is configured to instruct the MRI scanner to conduct a second set of N consecutive gradient readouts for the N second planes. In one embodiment, the imaging module is configured to construct a second 3D image frame using readout results of the second set of readouts. In another embodiment, the imaging module is configured to construct a third 3D image frame using the readout results of the last M of N second planes from the first set of readouts and the readout results of the first (N-M) of N second planes from the second set of readouts, M being an integer greater than 0 and less than N.

In one embodiment, the imaging module is configured to combine two 3D images representing co-registered perfusion images to construct a Cerebro-vascular Reserve (CVR) image based on the relation: CVR=(Stress−Rest)/Rest×100%.

Additionally, The MRI-based system also includes a quantification module configured to quantify levels of a patient's vascular reserve and construct a respective score representing each of the levels, wherein the quantification module is configured to implement the following calibration equation:

$$CBV_{SS} = WCF \times \frac{K_H}{\rho} \frac{[1/T_1^{pre-contrast} - 1/T_1^{post-contrast}]_{WM}}{[1/T_1^{pre-contrast} - 1/T_1^{post-contrast}]_{BloodPool}} \times (100 \text{ g/ml}).$$

wherein $CBV_{SS}$ refers to cerebral blood volume, wherein T1 refers to a rate of longitudinal regrowth of magnetization, wherein $T_1^{pre-contrast}$ refers to T1 before injection of an MRI contrast agent, wherein $T_1^{post-contrast}$ refers to T1 after the injection of an MRI contrast agent, wherein WM refers to that the $T_1^{post-contrast}$ and $T_1^{post-contrast}$ are measured simultaneously in the brain parenchyma of a subject, wherein BloodPool refers to that the $T_1^{pre-contrast}$ and $T_1^{post-contrast}$ are measured simultaneously in arterial blood of the subject, wherein $K_H$ is a dimensionless constant which corrects the measured T1 values by a ratio of blood hematocrit for differences between a perfusion bed and blood pool, wherein ρ refers to the density of the brain (roughly 1.04 gm/100 ml), and wherein WCF is a response curve which corrects raw values for $CBV_{SS}$ for effects of intra- to extra-vascular water exchange within the brain parenchyma.

In another aspect, the present disclosure relates to a method. In one embodiment, the method includes instructing an MRI scanner having a first axis and a first plane perpendicular to the first axis to conduct radial k-space samples having N second planes that each are perpendicular to the first plane and through which the first axis passes, N being an integer greater than 1, and instructing the MRI scanner with a 3D pulse sequence to generate a radio-frequency (RF) pulse, conduct a gradient readout in the first plane, and conduct a gradient readout in one of the N second planes.

In one embodiment, the method also includes instructing the MRI scanner to conduct an echo-planar readout along the first axis.

Further, the method may include instructing the MRI scanner to sample the k-space volume over a plurality of sample points sampling a line perpendicular to the first axis.

Moreover, the method also includes instructing the MRI scanner to acquire k-space samples through a 3D k-space volume at oblique angles so as to trace out samples oriented radially in the N second planes.

Additionally, the method includes comprising instructing the MRI scanner to conduct a first set of N consecutive gradient readouts for the N second planes.

In one embodiment, the method includes instructing the MRI scanner to have a raw sampling window about from 10,000 ms to 10 seconds.

In one embodiment, the method includes generating a first 3D image frame using readout results of the first set of readouts.

In one embodiment, the method includes acquiring images with a spatial resolution about 2.5 mm×0.825 mm×0.825 mm. In one embodiment, the method includes constructing 3D images at a rate of about 0.6 second/frame.

In one embodiment, the method includes instructing the MRI scanner to conduct a second set of N consecutive gradient readouts for the N second planes.

In one embodiment, the method includes generating a second 3D image frame using readout results of the second set of readouts.

In one embodiment, the method includes generating a third 3D image frame using the readout results of the last M of N second planes from the first set of readouts and the readout results of the first (N-M) of N second planes from the second set of readouts, M being an integer greater than 0 and less than N.

In one embodiment, the method includes combining two 3D images representing co-registered perfusion images to construct a Cerebro-vascular Reserve (CVR) image based on the relation: CVR=(Stress−Rest)/Rest×100%.

In one embodiment, the method includes quantifying levels of a patient's vascular reserve and generating a respective score representing each of the levels.

In one embodiment, the method includes quantifying the levels by implementing the following calibration equation:

$$CBV_{SS} = WCF \times \frac{K_H}{\rho} \frac{[1/T_1^{pre-contrast} - 1/T_1^{post-contrast}]_{WM}}{[1/T_1^{pre-contrast} - 1/T_1^{post-contrast}]_{BloodPool}} \times (100 \text{ g/ml}).$$

wherein $CBV_{SS}$ refers to cerebral blood volume, wherein T1 refers to a rate of longitudinal regrowth of magnetization, wherein $T_1^{pre-contrast}$ refers to T1 before injection of an MRI contrast agent, wherein $T_1^{post-contrast}$ refers to T1 after the injection of an MRI contrast agent, wherein WM refers to that the $T_1^{pre-contrast}$ and $T_1^{post-contrast}$ are measured simultaneously in the brain parenchyma of a subject, wherein BloodPool refers to that the $T_1^{pre-contrast}$ and $T_1^{post-contrast}$ are measured simultaneously in arterial blood of the subject, wherein $K_H$ is a dimensionless constant which corrects the measured T1 values by a ratio of blood hematocrit for differences between a perfusion bed and blood pool, wherein ρ refers to the density of the brain, and wherein WCF is a response curve which corrects raw values for $CBV_{SS}$ for effects of intra- to extra-vascular water exchange within the brain parenchyma.

These and other aspects of the present disclosure will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. The same reference numbers may be used throughout the drawings to refer to the same or like elements of an embodiment, wherein.

DETAILED DESCRIPTION

Figure 1:
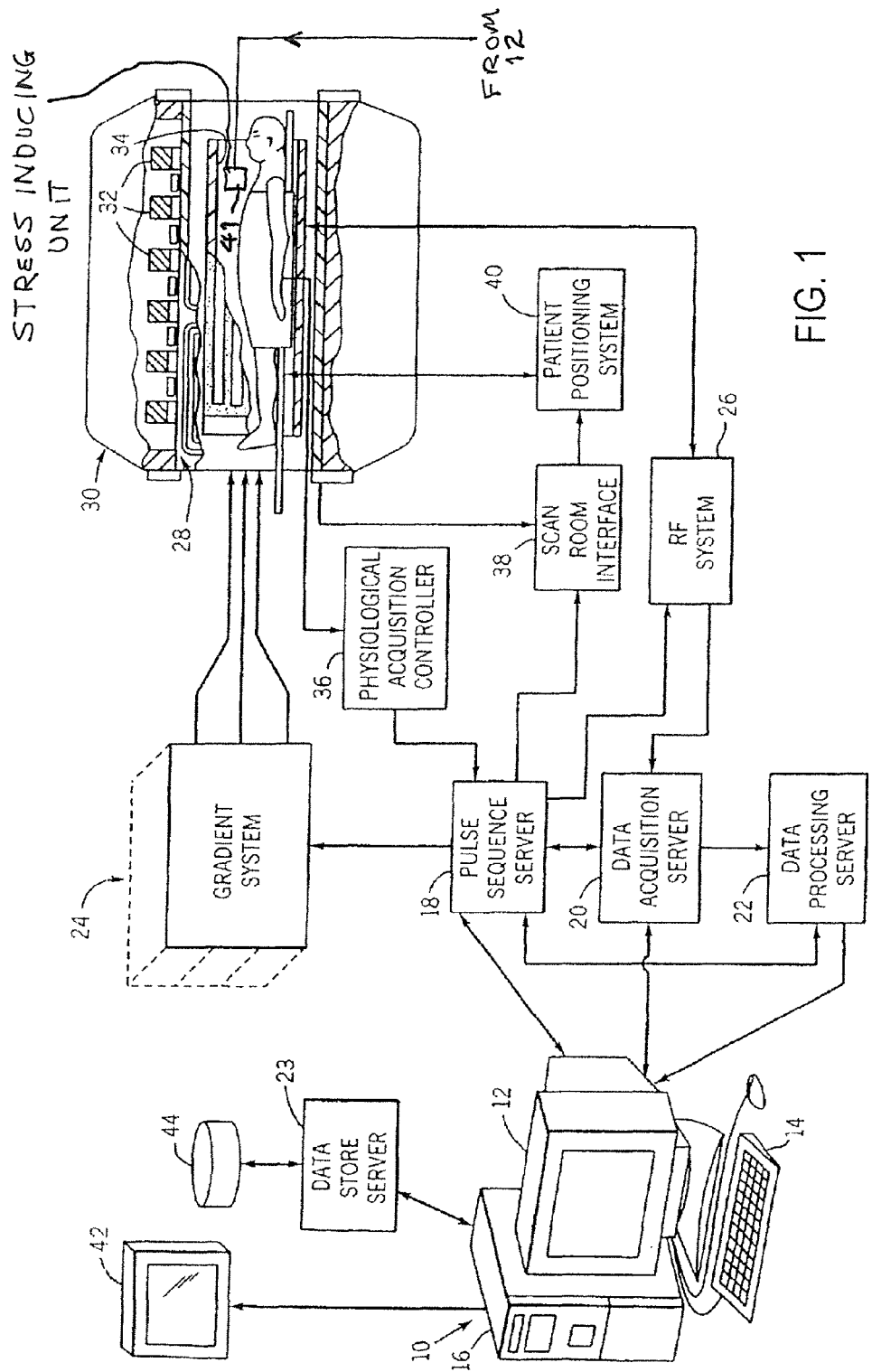
FIG. 1 is a block diagram of an MRI-based system in accordance with certain embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprising," "including," "carrying," "having," "containing," "involving," and the like are to be understood to be open-ended, i.e., to mean including but not limited to.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term "code", as used here, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

Referring particularly to FIG. 1, an MRI-based system in accordance with certain embodiments of the present disclosure is shown. The MRI-based system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI-based system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The server 18 is performed by a separate processor and the servers 20 and 22 are combined in a single processor. The workstation 10 and each processor for the servers 18, 20 and 22 are connected to an Ethernet communications network. This network conveys data that is downloaded to the servers 18, 20 and 22 from the workstation 10, and it conveys data that is communicated between the servers.

The pulse sequence server 18 functions in response to instructions downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients Gx, Gy and Gz used for position encoding NMR signals. The gradient coil assembly 28 forms part of a magnet assembly or MRI scanner 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components: $M=\sqrt{I^2+Q^2}$, and the phase of the received NMR signal may also be determined: $\phi=\tan^{-1} Q/I$.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates in response to instructions downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with instructions downloaded from the workstation 10. Such processing may include, for example: Fourier transformation of raw k-space NMR data to produce two or three-dimensional images; the application of filters to a reconstructed image; the performance of a back projection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

The key problem in the derivation of quantitative perfusion values is that of defining an appropriate scale factor that can convert the values of flow into physiologically meaningful perfusion (in ml of blood/gram of tissue/minute). Perfusion is normally reported as ml/100 g-minute. To determine this scale factor we have derived a MRI pulse sequence that uses a self-calibration technique. This requires a very rapid measurement of the longitudinal relaxation time, $T_1$, of the brain tissue to be performed.

Certain aspects of the present disclosure are directed to an imaging-based diagnostic test that can quantify cerebral vascular reserve (CVR). The current state of the art in the MRI of cerebral perfusion has several limitations, including: (1) Coarse Spatial Resolution: perfusion images have coarse spatial resolution of 1200-1500 mm2, compared to the 400-500 mm2 which is common in MRI angiograms of the head. (2) Insufficient Coverage: the superior/inferior coverage is currently limited to roughly half of the entire head with poor 5.0 mm resolution. (3) Sampling Rate is Insufficient: typical bolus transit times are 3-5 seconds, yet the current MRI scanners sample at 1-2 images per seconds. (4) Flow Reserve is Subjective: there is variable response to physiologic stress (a predictor of future stroke), and no accepted scoring system which would standardize evaluation across hospitals.

Arterial spin labeling (ASL) can be used for MRI quantification of perfusion. ASL images do not require the use of injected contrast agents, exposure to radiation. However, due to the lack of compartmentalization of the labeled water, it is typically impossible to quantify blood volume with ASL. Furthermore, ASL perfusion, while shown to be quantitative in healthy subjects, assume transit-time delays, T1 values and blood flow directions that are likely not met in a setting of sever atherosclerosis.

Using Relative CBF images that are available on most MRI scanners and represent an un-incalibrated image of cerebral perfusion can provide a so-called "stress test" of the vascular reserve is by.

Certain aspects of the present disclosure are directed to a diagnostic "stress test" that can be used to identify a patient's risk of stroke. Certain aspects of the present disclosure are directed to an imaging-based diagnostic test that quantifies CVR.

In certain embodiments, an MRI system identifies the degrees of hemodynamic impairment. Similar in principle to the cardiac stress test, measuring changes in cerebral perfusion in conjunction with a physiologic stress agent can serve as a metric which quantifies the degree of hemodynamic compromise. Acetezolemide (ACZ) is a carbonic anhydrase inhibitor penetrates the blood brain barrier and acts as a cerebral vasodilator. It is safe to administer is well tolerate by volunteers and patients. A standard intravenous dose of 1000 mg will induce a 30%-60% increase in CBF 10-15 minutes after administration.

In certain embodiments, a quantification module utilizing an imaging protocol to quantify cerebrovascular reserve (CVR) based on the results of MRI tests.

Certain aspects of the present disclosure are directed to an imaging-based diagnostic test that quantifies cerebral vascular reserve (CVR) and an MRI-based system for performing the test. Stated in a simplified way, the diagnostic test is, in certain aspects, analogous to the cardiac stress-test, which is used to assess the severity of coronary artery disease. In certain embodiments, an MRI-based system can assess the risk of stroke. In certain embodiments, an MRI-based imaging protocol and system quantifies physiologic changes induced by stress in the brain. This is similar, in a simplified manner and in certain aspects, the cardiac stress test commonly used by cardiologist to determine the risk of heart attack in patients with coronary artery disease.

In certain embodiments, an MRI-based system can employ one or more physical or functional modules to implement the functions, processes, or features described below.

In certain embodiments, an MRI-based system implementing a self-calibrating pulse sequence for image acquisition and a scoring system that can be used to standardize Cerebrovascular Flow Reserve (CFR). A pulse sequence is a series of events (or the computer program that initiates them) comprising RF pulses, gradient waveforms, and data acquisition. The purpose of the pulse sequence is to manipulate the magnetization in order to produce the desired signal.

In certain embodiments, a diagnostic tool aids in the prevention of stroke by quantifying the degree of hemodynamic compromise induced by the vascular disease and identifying subjects who would likely benefit from more aggressive therapy.

In certain embodiments, an MRI-based system utilizes an MRI pulse sequence to quantify cerbebral perfusion for longitudinal studies and determination of CVR. The system can identify the degree of hemodynamic impairment using MRI. Similar in a broader sense to the cardiac stress test, measuring changes in cerebral perfusion in conjunction with a physiologic stress agent can serve as a metric which quantifies the degree of hemodynamic compromise. Acetezolemide (ACZ) is a carbonic anhydrase inhibitor penetrates the blood brain barrier and acts as a cerebral vasodilator. It is safe to administer is well tolerate in patient studies. A standard intravenous dose of 1000 mg will induce a 30%-60% increase in CBF 10-15 minutes after administration.

Figure 2:
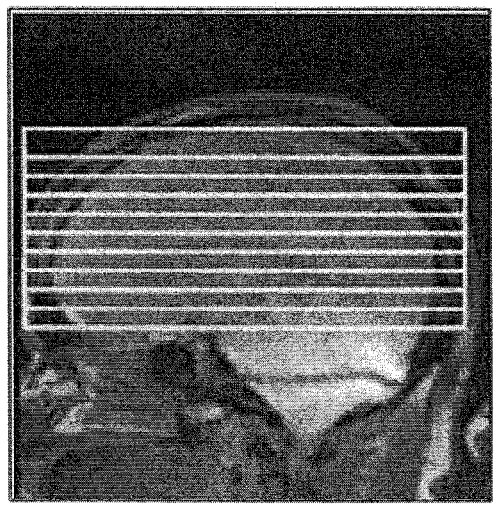
FIG. 2 schematically illustrates echo-planar readout and radial k-space samples used by an MRI-based system in accordance with certain embodiments of the present disclosure.
Figure 2:
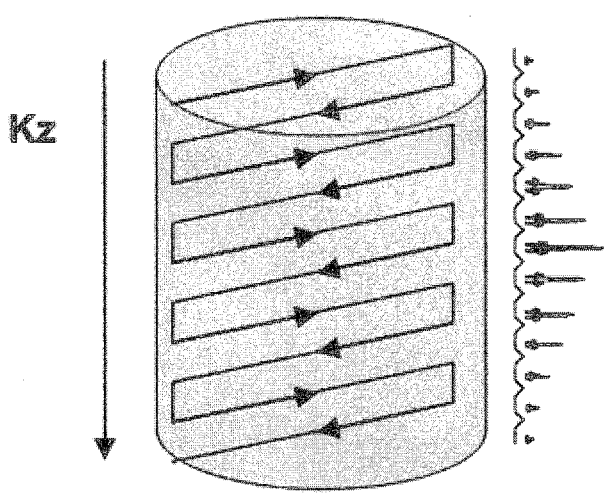
Figure 2:
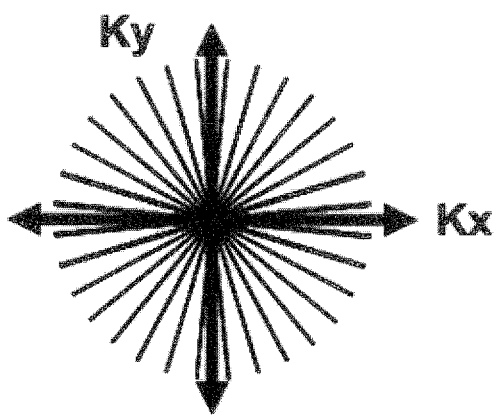
Figure 3:
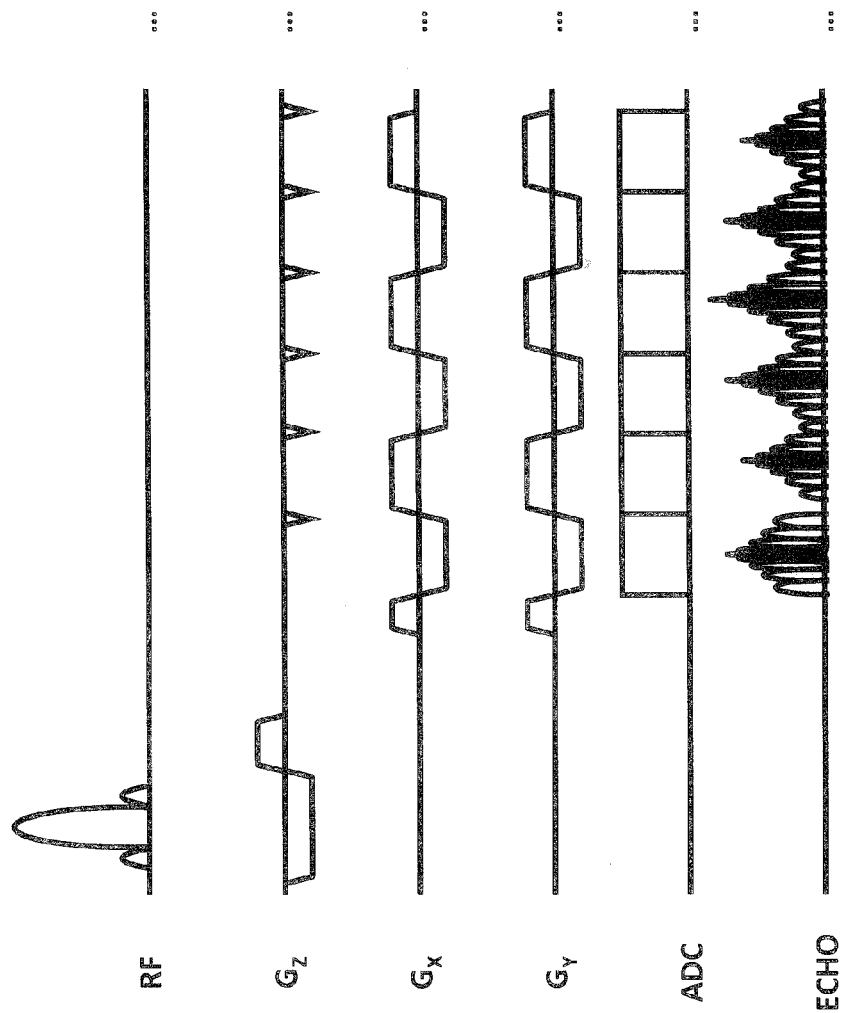
FIG. 3 schematically illustrates a Radial 3D Pulse Sequence used by an MRI-based system in accordance with certain embodiments of the present disclosure.

FIG. 2 schematically illustrates echo-planar readout and radial k-space samples used by an MRI-based system in accordance with certain embodiments of the present disclosure. FIG. 3 schematically illustrates a Radial 3D Pulse Sequence used by an MRI-based system in accordance with certain embodiments of the present disclosure. The MRI-based system uses a pulse sequence that samples in 3D using radial (as opposed to Cartesian) projections that will bisect the head and rotate in the right-left/anterior-posterior plane, with echo-planar readout in the superior-inferior direction. In other words, k-pace samples are acquired through the 3D k-space volume at oblique angles so as to trace out samples oriented radially with respect to the nominal $k_x$, $k_y$ plane so as to pass through the center of k-space on each echo. In certain embodiments, the MRI scanner has scan volume or a 3D k-space volume that has a first axis and one or more first planes perpendicular to the first axis. The scan volume or 3D k-space volume has N second planes that each are perpendicular to the first plane and through which the first axis passes, N being an integer greater than 1. The MRI scanner can sample, or evenly sample, the k-space volume over one or more sample points sampling a line perpendicular to the first axis. Moreover, the MRI scanner can sample, or evenly sample, the 3D k-space volume over a pluraility of radially samples trajectories about the first axis. Furthermore, the pulse sequence quantifies cerebral perfusion values such as capillary level cerebral blood flow (CBF, in ml/100 g/min), and cerebral blood volume (CBV, in ml/100 g). RF is the radio frequence pulse played out by the MRI scanner. Gz, Gx and Gy refer to the strength of the magnetic field gradients played on the X, Y and Z axes, respectively. ADC refers to the acquisition of MRI signal by the analog to digital converter. ECHO denotes the echo formed by the signal emitted from the object in the MRI scanner.

In certain embodiments, the sequence also acquires a single fixed projection in conjunction with a single in inversion recovery pulse to quantify the T1-mediated signal change in the blood pool and white matter.

Figure 4:
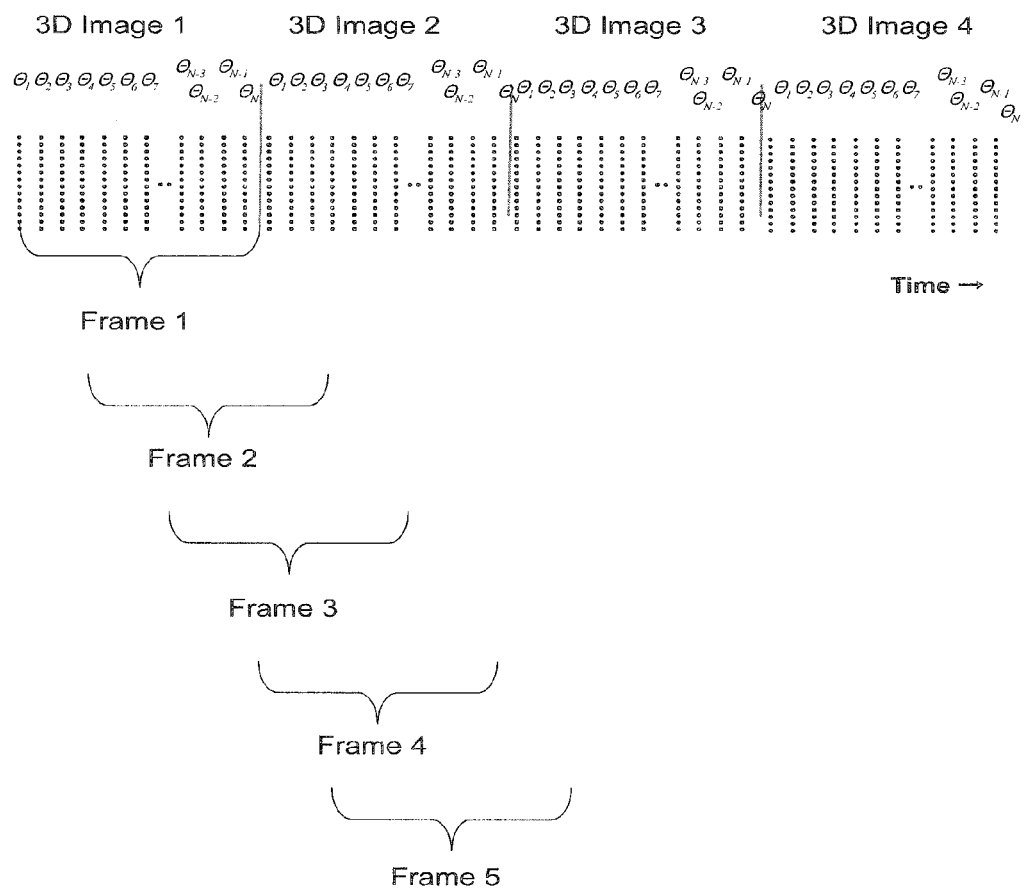
FIG. 4 schematically illustrates a sliding window view-sharing technique implemented by an MRI-based system in accordance with certain embodiments of the present disclosure.

FIG. 4 schematically illustrates a sliding window view-sharing technique implemented by an MRI-based system in accordance with certain embodiments of the present disclosure. The use of radial projections in the 3D image acquisition allows for sliding window view-sharing acquisitions. Typically a time series of 3D images (i.e. 3D Image 1, 3D Image 2, . . . etc.) are acquired to sample the passage of a bolus of contrast agent as it passes through the head. The signal changes are mathematically de-convolved to arrive at perfusion values. In the radial sliding window approach raw MRI images data (i.e. k-space data) from difference, but consecutive frames are combined to form an image with represents an intermediate time frame (Frame 1, Frame 2, Frame 3, etc.).

The reconstruction of multiple intermediate time frames allows for a higher apparent frame rate, finer temporal sampling of the contrast passage and T1 regrowth curve and more accurate perfusion values.

In a simplified example, the MRI scanner can acquire 5, 3D volumes, back-to-back in time. If each requires 10 seconds to acquire, the total time is 10 seconds/per volume time 5 volumes or 50 seconds. This would yield 5 samples, separated by 10 seconds of the aforementioned bolus kinetics. In certain example, the MRI based system "mixes" the image data to produce 3D images which form samples at a much higher rate than 10 seconds in the example. Through the "sliding window" reconstruction algorithm, the MRI based system can reconstruct a 3D image frame at less than, e.g., every 1-2 seconds. This 1-2 second threshold can be critical since the bolus passed through the head and it may be impossible to create perfusion images at a slower frame rate. In certain embodiments, a control module is configured to instruct the MRI scanner to conduct first and second sets of N consecutive gradient readouts for the N second planes. In one embodiment, an imaging module is configured to construct 3D image frames respectively using readout results of the first and second sets of readouts. In another embodiment, the imaging module is configured to construct a 3D image frame using the readout results of the last M of N second planes from the first set of readouts and the readout results of the first (N-M) of N second planes from the second set of readouts, M being an integer greater than 0 and less than N.

In certain embodiments, rather that acquiring a stack of 10-15 2D images of the brain at a spatial resolution of 5.0 mm×1.2 mm×1.2 mm (7.2 mm$^3$), the MRI-based system can acquire 64 images with a spatial resolution about 2.5 mm×0.825 mm×0.825 mm (1.6 mm$^3$). The acquired images are 3D volume images which typically cover the entire brain, including the infratentoral base of the brain. 3D imaging can have the advantages of improving the signal to noise ratio (SNR) of images in proportion to the square root of the imaging time. Normally acquiring high resolution images results in a loss of SNR since SNR is proportional to the volume of an imaging voxel. The use of 3D sampling provides the SNR needs to support a finer sampling matrix (i.e. higher resolution).

Using a Cartesian scheme, a 3D volume as described above, with a typically used echo time of 60 ms would require 3.84 seconds to acquire. This is a factor of 3-4 slower than the nominal 2D acquisition. In certain embodiments, the radial sampling scheme employed allows implementation of sliding window view-sharing image reconstruction. This allows acquisition of 3D volume images at about 0.6 sec/frame. The improved sampling of the contrast curves will improve the accuracy of time-base imaging metrics such as mean transit time which reflect perfusion pressure, and may serve as an independent measure of CVR.

The pulse sequence shown in FIG. 2 is used to yield 3D images of relative perfusion. That is, uncalibrated images. In certain embodiments, relative values are calibrated to quantitative values.

In certain embodiments, bookend calibration scans can be used for 2D perfusion images. The bookend calibration scans can measure the T1 changes in the blood pool and white matter, which are used to calibrate blood volume and perfusion. The bookend calibration is illustrated by the following equation:

$$CBV_{SS} = WCF \times \frac{K_H}{\rho} \frac{[1/T_1^{pre-contrast} - 1/T_1^{post-contrast}]_{WM}}{[1/T_1^{pre-contrast} - 1/T_1^{post-contrast}]_{BloodPool}} \times (100 \text{ g/ml}).$$

Whole brain perfusion is then calculated using the central volume principle as: qCBF=(qCBV$_{SS}$/rCBV$_{DSC}$)×rCBF. CBV$_{SS}$ refers to cerebral blood volume. qCBF refers to quantative cerebral blood flow. qCBV$_{SS}$ refers to quantitative cerebral blood volume in the steady-state. rCBVdsc refers to relative cerebral blood volume from Dynamic Susceptibility Contrast images. rCBF refers to relative Cerebral Blood Flow. T1 refers to the commonly used value of the rate of longitudinal regrowth of magnetization. The superscripts refer to this values before the injection of an MRI contrast agent (pre-contrast) or the values after the administration of the contrast agent (post-contrast), and these values are measure simultaneously in the brain parenchyma, i.e. in the white matter (WM), of the subject and in the arterial blood (BloodPool). Both of which can be properly defined as a post-processing step within the MRI images acquired within this technique. Kh is a dimensionless constant which is corrects the measured T1 values by the ratio of blood hematocrit for differences between the perfusion bed and blood pool (roughly 0.74). ρ refers to the density of the brain (roughly 1.04 gm/100 ml). WCF is a response curve which corrects the raw values for CBV$_{SS}$ for the effects of intra- to extra-vascular water exchange within the brain parenchyma.

The ability to quantify cerebral perfusion can be exemplified as disclosed in U.S. Pat. No. 8,099,149, which can allow for direct and quantitative determination of cerebrovascular reserve if measure prior to and under the influence of an appropriate physiologic challenge which can alter the normal perfusion values in the brain. The disclosure of U.S. Pat. No. 8,099,149 is incorporated herein in its entirety by reference.

From the reconstructed pre- and post-contrast T$_1$ maps a T$_1$ distribution is produced. Only the voxels that have a value within the full-width half-maximum of the largest peak of the T$_1$ distribution will be included in the segmented white matter map. Using the reconstructed T$_1$ maps, a correction factor for the effects of water exchange in the vasculature is calculated. The water correction factor is determined by:

$$WCF_{1.5T} = 8.2 \times 10^{-3} dR_{1,blood}^2 + 0.25 dR_{1,blood} + 0.51$$

$$WCF_{3T} = 9.5 \times 10^{-3} dR_{1,blood}^2 + 0.30 dR_{1,blood} + 0.52$$

where WCF$_{1.5T}$ is the water correction factor at 1.5 T, WCF$_{3T}$ is the water correction factor at 3.0 T, and $$dR_{1,blood} = (1/T_{1,blood}^{post} - 1/T_{1,blood}^{pre})$$

Next, an average value of steady state cerebral blood volume in the segmented white matter region (CBV$_{SS,WM}$) is calculated. First, CBV$_{SS,WM}$ is determined for each voxel in the segmented white matter region by:

$$CBV_{SS,WM} = \frac{1}{\rho} \times \left(\frac{1-H_{LV}}{1-H_{SV}}\right) \times \left(\frac{S_{Tissue}^{post} - S_{Tissue}^{pre}}{S_{Blood}^{post} - S_{Blood}^{pre}}\right)$$

where ρ is the average density in brain tissue (1.04 g/100 mL), H$_{LV}$ is a large vessel hematocrit having a value of 0.45, H$_{SV}$ is a small vessel hematocrit having a value of 0.25, S$_{Tissue}^{post}$ is the signal of the tissue in the reconstructed post-contrast T$_1$-weighted image, S$_{Tissue}^{pre}$ is the signal of the tissue in the reconstructed pre-contrast T$_1$-weighted image, S$_{Blood}^{post}$ is the signal of the selected blood pool in the reconstructed post-contrast $T_1$-weighted image, and $S_{Blood}^{pre}$ is the signal of the selected blood pool in the reconstructed post-contrast $T_1$-weighted image. From this calculation a distribution of the $CBV_{SS,WM}$ is determined. A measurement of the average $CBV_{SS,WM}$ can then be determined by fitting the $CBV_{SS,WM}$ distribution to a Gaussian distribution having the form:

$$Y = A \cdot e^{-\left(\frac{CBV_{SS,WM} - \langle CBV_{SS,WM}\rangle}{\sqrt{2}\sigma}\right)^2}$$

where Y is the distribution of $CBV_{SS,WM}$, A is a constant, $\langle CBV_{SS,WM}\rangle$ is the average steady state cerebral blood volume in the white matter region, and σ is the standard deviation of the steady state cerebral blood volume in the white matter region.

An average value of rCBV in the segmented white matter region is calculated. Finally, the quantitative CBF and CBV maps (qCBF and qCBV, respectively) are produced. The method of computing qCBV is as follows:

$$qCBV = \frac{1}{\rho} \times \left(\frac{1 - H_{LV}}{1 - H_{SV}}\right) \times \left(\frac{1/T_{1,Tissue}^{post} - 1/T_{1,Tissue}^{pre}}{1/T_{1,Blood}^{post} - 1/T_{1,Blood}^{pre}}\right)$$

where $1/T_{1,Tissue}^{post}$ is the $T_1$ value of the tissue in the post-contrast $T_1$ map, $1/T_{1,Tissue}^{pre}$ is the $T_1$ value of the tissue in the pre-contrast $T_1$ map, $1/T_{1,Vessel}^{post}$ is the $T_1$ value of the blood pool in the post-contrast $T_1$ map, and $1/T_{1,Vessel}^{pre}$ is the $T_1$ value of the blood pool in the pre-contrast $T_1$ map. The method for computing qCBF is given by:

$$qCBF = \frac{K_H}{\rho} \times WCF(dR_{1,blood}) \times \frac{\langle 1/T_1^{post} - 1/T_1^{pre}\rangle_{WM}}{dR_{1,blood}} \times \frac{rCBF}{\langle rCBV\rangle_{WM}}$$

where $K_H$ is a hematocrit correction factor having a value of 0.71, $WCF(dR_{1,blood})$ is the water correction factor calculated, $\langle 1/T_1^{post} - 1/T_1^{pre}\rangle_{WM}$ is the average rate of change of $T_1$ in the segmented white matter region, $dR_{1,blood}$ is the rate of change of $T_1$ in the blood pool as defined above, rCBF is the relative CBV value calculated, and $\langle rCBV\rangle_{WM}$ is the average rCBV in the segmented white matter region.

The method described above yields quantitative measurements of cerebral perfusion from imaging data acquired using an MRI system. Where previous quantitative measurements of cerebral perfusion were practically restricted to PET and CT imaging systems that expose the subject to be imaged to large doses of radiation, the present method uses no such radiation. Therefore, quantitative measurements of perfusion can be acquired through noninvasive means in a wider population. This is especially remarkable since the clinical uses of quantitative information relating to the perfusion process have substantial impact in numerous clinical diagnoses.

The form of the expression can depend on differences and ratios, making the calculation very robust against systematic errors in the determination of T1. In the 2D approach, the slice number, play and inversion pulse are fixed and a time-series of images at a fixed position to interrogate the relaxation curves are acquired. These T1-mediated relaxation curves are fit to the regrowth model to yield the T1 values used above.

In certain embodiments, a module of the MRI-based system can implement the 3D approach and perform accurate sampling of the T1-mediated longitudinal magnetization regrowth curve (M(t)~exp(−t/T1)). Typically T1's will change by 20-30 ms in white matter in response to the contrast agent injection. The 2D sequence is able to sample this curve in 84 ms increments over 1.2 seconds. The width of the sampling window is equal to the sampling increment and the product of the echo time and the number of acquired projections.

In certain embodiments, the MRI-based system employing the 3D pulse sequence has a raw sampling window of about from 10,000 ms to 10 seconds. The reconstruct intermediate time frames can be at frames of 1000 ms or less. The time scale for acquiring the image data can be much longer than the image frames eventually reconstructed. In certain embodiments, the MRI-based system uses a sliding window view-sharing reconstruction will be used.

An engineering challenge in the implementation of the 3D approach can be accurate sampling of the T1-mediated longitudinal magnetization regrowth curve (M(t)~exp(−t/T1)). Typically, T1's changes by 20-30 ms in white matter in response to the contrast agent injection. An 2D sequence is able to sample this curve in 84 ms increments over 1.2 seconds. The width of the sampling window is equal to the sampling increment and the product of the echo time and the number of acquired projections.

In certain embodiments, a module of the MRI-based system uses algorithms for segmentation of blood and white matter that are dependent on the shape of whole brain T1 distributions and not on manual drawing based on anatomic cues. In certain embodiments, a module of the MRI-based system can conduct quantitative perfusion reconstruction in coronal and sagittal planes.

in certain embodiments, a module of the MRI-based system can implement a score system quantifying levels of a patient's vascular reserve and provide physicians scores which can be used to evaluate and determine the level of a patient's vascular reserve. Deriving a quantitative value will allow periodic follow-up as well as to assess a patient's response to medical or surgical management. Co-registered perfusion images will be combined to yield CVR image based on the relation: CVR=(Stress−Rest)/Rest×100%. The rest/stress paradigm requires the induction of physiologic stress. There are a number of ways this can be achieved: simple breath-holding, respiration of $CO_2$ enhanced gas, or pharmacologically. Acetezolamide can be used to increase local perfusion. The size of the enhancement or depletion of perfusion will be quantified suing the MRI pulse sequence described above. For this purpose, as shown in FIG. 1, the MRI-based system includes a physiologic stress inducer 41, which interacts with the patient to induce stress of the type described above.

In certain embodiments, the MRI-based system can allow for scan-to-scan perfusion changes to be determined. By utilizing physiologic stress between to consecutive perfusion scans, the MRI-based system can quantify the ability of an individual to augment perfusion (i.e. the flow reserve). Using a simple difference of ratio images, the MRI-based system can produce whole head, quantitative CFR images.

Inter-compartmental water exchange (between vascular and extravascular spaces) can be different on the first and second MRI scans. In certain embodiments, a module of the MRI-based system can implement Monte Carlo analysis to determine the effects of the second injection. The residual Gd from the rest exam has the potential to induce variability in the stress perfusion exam. Therefore signal changes associated with water exchange in the stress scans need to be explicitly calculated and verified. The Monte Carlo module simulates changes in blood-pool and white matter T1, intra-to-extravascular water exchange rates and blood volume and how these bias CBV quantification. The water exchange rate in the human brain can be thus determined. The WCF for 1.5 T and 3.0 T perfusion scans has been determined, assuming an initial T1 of unenhanced blood. An analysis can be conducted by fixing the exchange rates to the values and varying blood volume pre- and post Blood T1 values. The T1 values can be chosen to represent pre- and post Gad injections for a two injection protocol that apportions 0.2 mmol/kg of gadolinium into 2 injections. The proposed simulations can provide calibration curves for a range of injection protocols that will guide the Diamox stress exam. It is, in certain circumstances, anticipated that a large fraction of the total dose is to be spilt to the stress exam to mitigate the effects of the rest exam.

In certain embodiments, the MRI-based system implements a score system representing levels of vascular reserve and can provide physicians a score which can be used to evaluate determine the level of a patient's vascular reserve. Deriving such quantitative value system can allow periodic follow-up as well as to assess a patient's response to medical or surgical management.

In certain embodiments, the MRI-based system generates CVR images and scoring based on images acquires in the second arm of the test-retest/sensitivity analysis study. Co-registered perfusion images will be combined to yield CVR image based on the well known relation: CVR=(Stress−Rest)/Rest×100%.

In certain embodiments, the white matter and blood T1 values can be compared directly as well as MTT. The MTT could be biased due to the broader sampling window of the 3D scan. MTT values are compared where the SWF is systematically altered to determine whether this is the source of the error. Other approaches to reduce the "temporal footprint" of the 3D scan such as radial parallel imaging or compressed sensing approaches can be implemented.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A magnetic resonance imaging (MRI) system, comprising:
   an MRI scanner that has a first axis and a first plane perpendicular to said first axis, and that comprises a radio-frequency (RF) antenna arrangement and a gradient coil arrangement;
   a control computer configured to operate the MRI scanner in a first execution of a 3D pulse sequence to radiate an RF pulse with said RF antenna arrangement to produce a first excitation of nuclear spins in an examination subject and to thereafter acquire first raw data from the examination subject representing magnetic resonance signals produced by said first excitation of said nuclear spins, and to generate magnetic gradient fields with said gradient coil arrangement that cause respective samples of said first raw data to be entered into 3D k-space in N second planes that are each perpendicular to said first plane and through which said first axis passes, with said N second planes thereby being radial planes in 3D k-space, with N being an integer greater than 1, thereby producing a first set of 3D k-space data;
   a stress-inducing unit configured to interact with the examination subject in the MRI scanner to induce a physiological stress in the examination subject after acquiring said first 3D k-space data set;
   said control computer being configured to operate the MRI scanner to execute a repetition of said 3D pulse sequence, including radiating a second RF pulse, after inducing said physiological stress in the examination subject, to produce a second excitation of nuclear spins in the examination subject, and to enter samples of second raw data, resulting from said second excitation, into 3D k-space in said N second planes, thereby producing a second 3D k-space data set;
   an image reconstruction computer provided with said first 3D k-space data set and said second 3D k-space data set, and configured to reconstruct a first image of the examination subject from said first 3D k-space data set and to reconstruct a second image of the examination subject from said second 3D k-space data set;
   said image reconstruction computer being configured to bring said first image and said second image into registration with each other and to identify at least one cerebral blood indicator, selected from the group consisting of cerebral blood flow and cerebral blood volume, in said first image and said second image in registration with each other and to reconstruct a cardiovascular reserve (CVR) image as a quotient having a numerator which is a difference of said at least one cerebral blood indicator in said first image subtracted from said at least one cerebral blood indicator in said second image, and a denominator which is said cerebral blood indicator in said first image multiplied by 100%; and
   said image reconstruction computer being configured to make said CVR image available at an output of said image reconstruction computer in electronic form, as a data file.

2. The MRI system of claim 1, wherein the quantification module is configured to implement the following calibration equation:

$$CBV_{SS} = WCF \times \frac{K_H}{\rho} \frac{[1/T_1^{pre-contrast} - 1/T_1^{post-contrast}]_{WM}}{[1/T_1^{pre-contrast} - 1/T_1^{post-contrast}]_{BloodPool}} \times (100 \text{ g/ml}),$$

wherein CBVss refers to cerebral blood volume,
wherein T1 refers to a rate of longitudinal regrowth of magnetization,
wherein $T_1^{pre-contrast}$ refers to T1 before injection of an MRI contrast agent,
wherein $T_1^{post-contrast}$ refers to T1 after the injection of the MRI contrast agent,
wherein WM refers to that the $T_1^{re-contrast}$ and $T_1^{post-contrast}$ are measured simultaneously in a brain parenchyma of a subject,
wherein BloodPool refers to that the $T_1^{pre-contrast}$ and $T_1^{post-contrast}$ are measured simultaneously in arterial blood of the subject,
wherein $K_H$ is a dimensionless constant which corrects the measured T1 values by a ratio of blood hematocrit for differences between a perfusion bed and blood pool,
wherein ρ refers to a density of a brain, and
wherein WCF is a response curve which corrects raw values for CBVss for effects of intra- to extra-vascular water exchange within the brain parenchyma.

3. An MRI system as claimed in claim 1 wherein said control computer is configured to operate said gradient coil arrangement of said MRI scanner in said 3D pulse sequence to generate said gradient magnetic fields to produce a sampling window in said 3D pulse sequence, in which said samples of said first raw data are acquired and to produce a sampling window in said repetition of said 3D pulse sequence, in which said samples of said second raw data are acquired, with each sampling window having a duration in a range between 10,000 ms and 10 seconds.

4. An MRI system as claimed in claim 1 wherein said control computer is configured to operate said MRI gradient coil arrangement of said scanner in said 3D pulse sequence, and in said repetition of said 3D pulse sequence, to generate said gradient magnetic fields to respectively acquire said samples of said first raw data of said first raw data and said samples of said second raw data each with a spatial resolution of about 2.5 mm×0.825 mm×0.825 mm.

5. An MRI system as claimed in claim 1 wherein said control computer is configured to operate said MRI scanner, and said image reconstruction computer is configured to reconstruct said first image and said second image, so as to cause said first image and said second image to be reconstructed at a rate of about 0.6 second/image.

* * * * *

UNITED STATES PATENT AND TRADEMARK OFFICE
CERTIFICATE OF CORRECTION

PATENT NO.        : 9,140,771 B2
APPLICATION NO.   : 13/405126
DATED             : September 22, 2015
INVENTOR(S)       : Timothy J. Carroll et al.

It is certified that error appears in the above-identified patent and that said Letters Patent is hereby corrected as shown below:

In the specification,

In the STATEMENT AS TO RIGHTS UNDER FEDERALLY-SPONSORED RESEARCH:

At column 1, line number 21 "RO NS049395-01" should be deleted and --R01 NS049395-- should be inserted in its place.

Signed and Sealed this
Fifth Day of April, 2016

Michelle K. Lee
*Director of the United States Patent and Trademark Office*